United States Patent [19]

Cremers et al.

[11] 4,447,153

[45] May 8, 1984

[54] APPARATUS AND METHOD FOR QUANTITATIVE MEASUREMENT OF SMALL DIFFERENCES IN OPTICAL ABSORPTIVITY BETWEEN TWO SAMPLES USING DIFFERENTIAL INTERFEROMETRY AND THE THERMOOPTIC EFFECT

[75] Inventors: David A. Cremers; Richard A. Keller, both of Los Alamos, N. Mex.

[73] Assignee: The United States of America as represented by the United States Department of Energy, Washington, D.C.

[21] Appl. No.: 386,371

[22] Filed: Jun. 8, 1982

[51] Int. Cl.$^3$ .............................................. G01B 9/02
[52] U.S. Cl. ..................................................... 356/361
[58] Field of Search ........................................ 356/361

[56] References Cited

U.S. PATENT DOCUMENTS 4,229,105 10/1980 Silverbage ...................... 356/361 X

OTHER PUBLICATIONS

Cremers et al., "Optical Nulling for Trace Analysis Based on the Thermooptic Effect and an Interferometer", Abstract THMII in the Technical Digest of the CLEO '81 Conference on Lasers and Electro-Optics, Washington, D.C., Jun. 10–12, 1981, Digest date unknown.

Cremers et al., "Thermooptic-Based Differential Measurements of Weak Solute Absorptions with an Interferometer", *Applied Optics*, vol. 21, No. 9, pp. 1654–1662, May 1982.

Cremers et al., "Quantitative Measurement of Solute Absorption at Levels Below Solvent Absorption by Optical Nulling Techniques", Abstract A305 in Advance Program of the Los Alamos Scientific Laboratory Conference on Optics '81, Los Alamos and Santa Fe, N.M., Apr. 7–10, 1981, date of advance program unknown.

Stone, "Measurements of the Absorption of Light in Low-Loss Liquids", *J. Opt. Soc. Am.*, vol. 62, No. 3, pp. 327–333, Mar. 1972.

*Primary Examiner*—William L. Sikes
*Assistant Examiner*—Matthew W. Koren
*Attorney, Agent, or Firm*—Samuel M. Freund; Paul D. Gaetjens; Michael F. Esposito

[57] ABSTRACT

An apparatus and method for the measurement of small differences in optical absorptivity of weakly absorbing solutions using differential interferometry and the thermooptic effect has been developed. Two sample cells are placed in each arm of an interferometer and are traversed by colinear probe and heating laser beams. The interrogation probe beams are recombined forming a fringe pattern, the intensity of which can be related to changes in optical pathlength of these laser beams through the cells. This in turn can be related to small differences in optical absorptivity which results in different amounts of sample heating when the heating laser beams are turned on, by the fact that the index of refraction of a liquid is temperature dependent. A critical feature of this invention is the stabilization of the optical path of the probe beams against drift. Background (solvent) absorption can then be suppressed by a factor of approximately 400. Solute absorptivities of about $10^{-5}$ cm$^{-1}$ can then be determined in the presence of background absorptions in excess of $10^{-3}$ cm$^{-1}$. In addition, the smallest absorption measured with the instant apparatus and method is about $5 \times 10^{-6}$ cm$^{-1}$.

29 Claims, 6 Drawing Figures

APPARATUS AND METHOD FOR QUANTITATIVE MEASUREMENT OF SMALL DIFFERENCES IN OPTICAL ABSORPTIVITY BETWEEN TWO SAMPLES USING DIFFERENTIAL INTERFEROMETRY AND THE THERMOOPTIC EFFECT

This invention is the rusult of a contract with the Department of Energy (Contract No. W-7405-ENG-36).

BACKGROUND OF THE INVENTION

The present invention relates generally to the use of a differential interferometer to measure small differences in optical absorptivity between two weakly absorbing samples located therein, and more particularly to the use of the chanqe in refractive index of a weakly absorbing sample due to the heat generated when an intense laser beam traverses it relative to a second irradiated sample of slightly different optical absorptivity, each of which is positioned in one arm of an interferometer cavity, which change produces a fringe pattern shift which can be related to the difference in optical absorptivity of the samples.

In many instances the detection of trace amounts of dissolved material is complicated by large background absorptions of the solvent. Under such conditions the part of the absorption signal due to the solute can be much smaller than the precision of the measurement of the combined solvent and solute absorption in which case no useful concentration information can be obtained using conventional measurement technology. The apparatus and method of the instant invention allows the solvent absorptivity to be nulled out of the measurements, the resulting absorption related signal being related solely to the solute absorptivity. A cell containing a weakly absorbing solution is placed in each arm of an interferometer. Heat is generated when a laser beam traverses the cells since a certain fraction of its energy is absorbed by the sample causing an increase in temperature. This results in a change in the index of refraction of the solution which is temperature dependent with a consequent change in the optical pathlength of the laser beam through the cell. Such changes in pathlength can be measured with an interferometer. For low-loss media (losses of $10_{-4} cm^{-1}$ or less), this effect is very small, and sensitive interferometers in well-controlled environments must be employed. For solutions having the same absorptivity, and for heating beams of equal intensity, the change in optical pathlength produced by laser heating is the same in each cell, and there is no shift in the fringe pattern formed by the interferometer. However, any difference between the absorptivities of the two solutions results in unequal heating and a fringe pattern shift. The degree of fringe movement is a measure of the difference in absorptivity between the two cells. A critical feature of the instant invention, which allows clear resolution of differences in sample absorptivity of approximately $10^{-5} cm^{-1}$, is that two fringe patterns are formed using laser beams from the interferometer. A signal fringe pattern is formed by a pair of low-power helium-neon laser beams each of which traverses a sample cell colinearly with a heating laser beam. A reference fringe pattern is formed from another pair of low-power helium-neon laser beams passing through the sample cells narrowly displaced from the heating beams. The purpose of this latter fringe pattern is to stabilize the signal fringe pattern with respect to normal thermal drift. This stabilization is achieved using a movable compensator plate inside the interferometer controlled via a feedback loop which has as its input the fringe pattern intensity at a fixed point which is a measure of the fringe position. It is this stabilization which allows the achievement of the minimum detection limits to be reported hereinbelow, and which represents a significant improvement over that which can be achieved by other methods where the solvent absorptivity is in the range of about $10^{-3} cm^{-1}$ or higher using the instant invention. Signals due to solvent absorptivity have been nulled to approximately one part in four hundred which thereby allows the clear resolution of absorptivity differences of about $10^{-5} cm^{-1}$ using about 50 mW of laser power. For comparison in the nondifferential configuration of the instant interferometer; that is, a sample cell in only one arm, and with a background absorption of $10^{-3} cm^{-1}$, the minimum detectable change in solute absorption is approximately $10^{-4} cm^{-1}$ in the best cases. The decrease in minimum detection limit which occurs with differential detection is due principally to the increased precision of the data relative to that obtained using nondifferential techniques.

Although interferometers (refractometers) have been used for over one hundred years to compare the refractive indices of gases, the use of an interferometer to detect weak absorptions using the thermooptic effect was only recently demonstrated.

1. In "Measurements of the Absorption of Light in Low-Loss Liquids," by J. Stone, J. Opt. Soc. Amer. 62, 327 (1972), the author describes a dual-beam interferometer where an intense laser light beam simultaneously heats the single solution under investigation and monitors its change in optical pathlength due to heating and thermal drift, while another laser beam of weak intensity monitors any changes in optical pathlength due to thermal drift alone. Both beams in Stone's apparatus are separated by only a few millimeters and traverse the same solution so that the change in optical pathlengths from drift recorded by the beams are equal. In this way the fringe pattern was stabilized with respect to drift and small shifts in this pattern due to heating could readily be measured. The apparatus could not, however, be used for differential measurements since the fringe pattern is not stabilized if both beams are used to record the thermooptic signal from different solutions. This is the critical feature of the instant invention, not taught by Stone. Our invention teaches the use of a drift stabilizing reference laser beam in each of two sample cells for which the difference in absorptivities is being determined, the stabilization of the fringe pattern resulting therefrom leading to significantly enhanced measurement sensitivity. The instant invention, then, teaches the measurement of changes in refractive index of the two sample solutions due to heating using weak intensity probe laser beams colinear with heating laser beams. Thermal drift in the probe fringe pattern is reduced by the use of a reference set of fringes formed from low-intensity reference laser beams which pass through the sample solutions slightly displaced from the probe and heating beams. A driven compensator plate inside our interferometer is connected to a feedback loop which responds to error signals resulting from thermal drift, which signal is used to keep the reference fringe pattern stable. The drift in the probe fringes was found to be identical to that of the reference fringes due to the proximity of the two sets of beams so that both sets of fringes could be stabilized in this manner, without which the reported sensitivity could not have been achieved.

2. In "Optical Nulling for Trace Analysis Based on The Thermooptic Effect and an Interferometer," by David A. Cremers and Richard A. Keller, Advance Program of the Conference on Lasers and Electrooptics, Washington, D.C., June 10–12, 1981, distributed sometime in April, 1981, and in "Quantitative Measurement of Solute Absorption at Levels Below Solvent Absorption by Optical Nulling Techniques," by D. A. Cremers and R. A. Keller, Los Alamos Conference on Optics '81, Santa Fe, NM, Apr. 6–9, 1981, the authors, who are also inventors of the instant invention, briefly describe the invention in abstract form. However, although both references mention the differential nulling procedure, neither even hints at the fringe stabilization critical in attaining the minimum detection limit quoted hereinabove.

An object of the instant invention is to measure small differences in optical absorptivity between two weakly absorbing samples.

Another object of our invention is to determine the concentration of a solute in solution where the solute absorptivity is much smaller than that of the solution.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention may comprise an interferometer cavity into which is placed two cells containing the samples under investigation, narrowly-spaced probe and reference laser beams which are each split into two widely-spaced, parallel beams after entry into the cavity, one probe beam and one reference beam becoming narrowly-spaced and parallel before entering one of the sample cells, and the other probe and reference beams becoming similarly narrowly-spaced and parallel before entering the second of the cells, the two probe and two reference laser beams being recombined to form a probe and reference fringe pattern, respectively, two amplitude modulated heating laser beams, means for equalizing their intensity and rendering them colinear with the split probe laser beams, one with each, and means for separating them from the probe beams after they exit the sample cells, means for equalizing the intensity and adjusting the parallelism of the two beams in each of the probe and reference beam pairs, means for stabilization of the reference and probe fringe patterns, and means for detecting and recording the probe fringe pattern intensity. Preferably, the interferometer cavity is of the Jamin design in order to reduce sensitivity of the apparatus to vibrations. It is also preferred that the probe and reference laser beams incident upon the interferometer cavity derive from a single laser source the output of which is divided into two approximately equal intensity parts. Similarly, it is preferred that the heating laser beams derive from a single laser source, the output of which is divided into two approximately equal intensity parts. It is further preferred that each pair of narrowly-spaced probe and reference laser beams be located approximately 5 mm apart. It is finally preferred that the means for stabilizing the reference fringe pattern include a movable compensator plate which is part of a closed feedback loop which further includes means for dithering and driving the plate to provide modulation and adjustment of the fringe pattern necessary for phase-sensitive detection. The compensator plate intersects the probe and reference beams in one arm of the interferometer so that the shift in probe fringes due to a thermooptic-induced response of the interferometer is also modulated at the same frequency as the reference fringes and can be monitored by phase-sensitive detection.

In a further aspect of the present invention, in accordance with its objects and purposes, the method hereof may also comprise splitting incident parallel probe and reference laser beams into a pair of probe and reference laser beams, each widely spaced split probe beam of approximately equal intensity traveling in a parallel direction, and similarly for the split reference beams, one probe and one reference beam emerging narrowly-spaced, and similarly for the second probe and reference beam, inserting a light-transmitting sample holding cell in the path of each pair of laser beams, recombining the two probe beams and the two reference beams to form probe and reference fringe patterns, respectively, introducing the samples under investigation into the cells, superimposing an amplitude modulated heating laser beam to be colinear with each probe laser beam before it enters the sample cell for a specified period of time, each of these heating beams having substantially the same intensity, separating the laser heating beam from each probe beam after each pair has passed through one of the sample cells, stabilizing the reference fringe pattern with respect to drift due to air currents, variations in room temperature, and thermal gradients in the sample cells thereby simultaneously stabilizing the probe fringe pattern, monitoring the probe fringe pattern for movement during the time that the heating laser beams pass through the sample cells, differences in absorptivity of the contents of the cells causing different degrees of heating in each cell as a result of the thermooptic affect thereby changing the refractive index of that cell's contents and consequently its optical pathlength for the probe beam traversing it which in return varies the fringe pattern position, establishing the relationship between the difference in absorptivity of the two samples and the position of the probe fringe pattern with samples of known absorptivity, and relating the position measured for the samples under investigation to a value of this difference in absorptivity. It is preferred that two pairs of narrowly-spaced probe and reference laser beams be separated by about 5 mm in order that the stabilization of the reference fringe pattern will simultaneously stabilize the probe fringe pattern. It is also preferred that the specified period of heating be approximately 10s followed by an approximately 1 min. period of cooling before another heating period and measurement of the consequent probe fringe pattern intensity change is commenced. Preferably, the probe and reference laser beam splitting and recombining steps are performed using a Jamin-type interferometer in order to make the sensitivity of the absorptivity difference measurements to vibrations minimal. It is finally preferred that the stabilizing of the reference fringe pattern position be accomplished using a fringe position detector, feedback electronics, and a driven compensator plate which intercepts one pair of probe and reference beams.

In summary, then, an apparatus and method for the measurement of small differences in optical absorptivity of weakly absorbing samples using differential interferometry and the thermooptic effect has been developed. The critical feature of our invention is the stabilization against drift of the optical pathlength of the probe laser beams which interrogate the samples under investigation, which differential change in pathlength is related to the absorptivity difference between the samples. It is thereby possible to null out the bulk of the sample absorptivity and measure only this difference with substantial precision. Solute absorptivities of $10^{-5}$ cm$^{-1}$ have been measured in solutions with total absorptivity in excess of $10^{-3}$ cm$^{-1}$ which is not possible with non-differential methods. Further, the smallest absorption measured with our invention was about $5 \times 10^{-6}$ cm$^{-1}$, which is comparable to or below measurements made using other thermooptic techniques. The principal advantages of the instant invention include low detection limits, only one critical alignment—that of the superposition of the probe and heating laser beams, simple analysis of the data, insensitivity to small variations in laser beam profile since the technique does not depend on the formation of a thermal lens, and easily obtained differential thermooptic spectra of solutions. This last use of our invention involves the use of separate probe and heating beams to record the thermooptic signal which permits scanning of the heating wavelength without the problem of phase shifts introduced by dispersion in optical elements through which the beams pass. Since the wavelength of the probe beam is fixed, a phase shift occurs only due to heating of the solutions.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
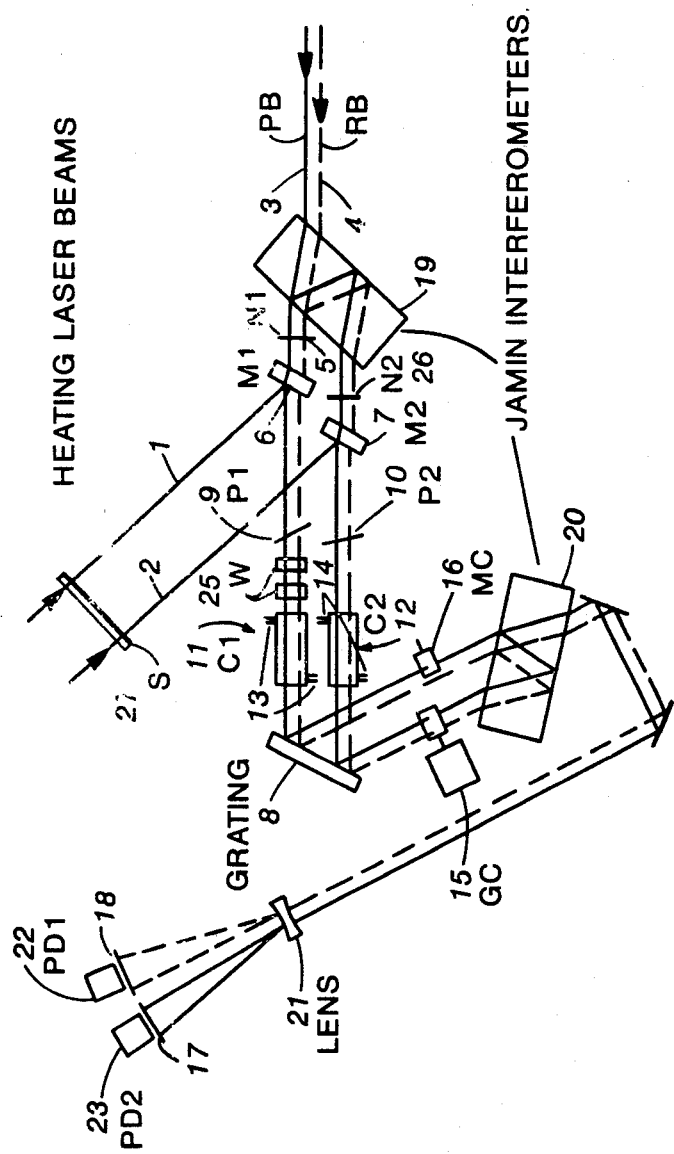
FIG. 1 is a schematic diagram of the apparatus used for differential measurements of weak sample optical absorptions wherein the samples under investigation are located in an interferometer cavity and the thermooptic effect produces a shift in the output fringe pattern of the interrogating probe beams which can be related to the difference in the two sample absorptivities when heating laser beams of equal intensity traverse the samples colinear with the probe beams.

FIG. 1 is a schematic representation of the apparatus used for the differential measurements reported for the instant invention. The heart of this apparatus is a commercial interferometer of a Jamin design which consists principally of two optically flat glass blocks 19, 20. Two laser beams 3, 4, are incident on the first glass block 19, each being split into two beams. Most usually, the two incident beams hereinafter labelled probe beam 3 and reference beam 4, will be split off as approximately equal intensity beams from a single laser source. The incident and exit surfaces of the glass blocks are reflection coated such that the two beams in the interferometer formed from each of the incident laser beams have about the same intensity when they emerge from the splitting block. After passing through various optical components in the interferometer, the beams are recombined in the second glass block 20 to form two interference fringe patterns. Any differential change between the optical pathlengths of the two beams in the interferometer results in a fringe shift. The Jamin design was chosen because of its reduced sensitivity to vibrations compared to other types of interferometers. The probe beam and the reference beam are low-power helium-neon laser beams (approximately 1 mW), separated by approximately 5 mm. The split probe beam, designated by the solid line, emerges from the first interferometer block as two parallel laser beams of approximately equal intensity, which form two arms of the interferometer. Intensities of the two probe beams are adjusted to be substantially equal using neutral density filters 5, 26 to give maximum fringe visibility on recombination. Similarly, the reference laser beams are split into parallel beams of approximately equal intensity which are represented by the dashed lines in FIG. 1, one of the split reference beams lying parallel and narrowly-spaced from one of the probe beams, while the other reference beam emerges parallel and narrowly-spaced to the second of the probe beams. The two arms of the interferometer, which will be designated as the upper arm and the lower arm, are widely separated. The two emerging reference beams are made to be of substantially equal intensity using neutral density filters 5, 26, again for the purpose of giving maximum fringe visibility upon recombination of these beams. Two laser heating beams 1, 2 are made colinear with the split probe beams, one with each, using dielectric coated mirrors 6, 7 (2.5 cm dia.$\times$0.95 cm thick, 99% reflectivity at 515 nm, 66% transmission at 633 nm). In the instant invention, the two heating beams are derived from a single argon-ion laser operating at 515 nm the output of which was split into two approximately equal beams. The intensities of the two heating beams were made substantially equal before entering sample cells 11, 12 by rotating thin glass plates 9, 10 to control the amount of light reflected out of each beam. A pair of wedged quartz plates (30' wedge) 25 were positioned in the upper arm to correct for any deviation of the beams from nonparallel paths through the interferometer introduced by other wedged optical elements (e.g., cell windows). These wedged plates were necessary to insure that the helium-neon laser beams recombined in the second glass block are colinear when they are merged. Two 5 cm long spectrometer sample cells 11, 12 are inserted into the two arms of the interferometer, one into each arm, in such a way that one set of three laser beams traverses each (the probe beams colinear with the heating beams and the two reference beams approximately 5 mm away from the heating beams). A diffraction grating 8 located after the sample cells separates the heating and probe beams. In this way, the heating beams do not pass through the glass blocks forming the interferometer, eliminating problems associated with heating of the glass blocks which may lead to an unwanted thermally-induced probe fringe shift. The helium-neon probe and reference laser beams in the lower arm of the interferometer then pass through a galvanometer-driven compensator plate 15 that was part of a closed feedback loop used to stabilize the reference fringe pattern with respect to drift due to air currents, variations in room temperature and thermal gradients in the samples. This compensator was dithered to provide modulation of the fringe pattern position necessary for phase-sensitive detection. Other components of the feedback loop were the galvanometer control electronics, a lock-in amplifier, and a photodiode. Fringe stabilization was necessary because the measurements reported here involve the detection of fringe shifts due to changes in optical pathlengths as small as about 1/200 of the helium-neon wavelength. Stabilization was achieved using the principle also used by the author of reference 1 who noted that drifts in the probe and reference fringes are equal if the beams in the interferometer travel over approximately the same paths. This has been found to be the case in our interferometer for probe and reference beams in each arm separated by approximately 5 mm. Therefore, stabilization of the reference fringes with the galvanometer-driven compensator also stabilize the probe fringes. The probe laser beam in the upper arm passes through a manually operated compensator plate 16 which permits independent adjustment of the optical pathlength of this beam through the interferometer. The four helium-neon beams then enter the second glass block 20 of the interferometer and are combined into two fringe patterns. Each set of fringes was expanded by a negative lens 21 to approximately 4 cm diameter and observed on one of two screens 17, 18. Typically, two or three complete fringes could be seen on the screen. The positions of the fringe patterns can be determined by monitoring these intensities at points on the screens through small holes (1.1 mm dia.) using photodetectors 22, 23. The entire apparatus was shielded from room air currents by a clear-plastic cover.

The shift in probe fringes due to the thermooptic-induced response of the interferometer which is related to the difference in optical absorptivity of the two samples was monitored using a photomultiplier tube 23 and a second lock-in amplifier tuned to the dither frequency of the compensator plate 15. Entrance and exit ports 13, 14 on the sample cells permit measurements on flowing samples. Heating of the solutions was initiated by opening a shutter 27 that blocked the argon-ion laser beam. Prior to measurement of the fringe shift, a check was made to insure that a minima of the fringe pattern was centered over the hole in the screen (approximately 0 V lock-in amplifier signal). Generally, resetting of the probe fringe pattern using the manual compensator 16 to put a probe fringe minimum over the hole in the screen was not necessary because relative drift of the reference and probe fringes was long-term (approximately 1 hour). Immediately before opening the shutter, the lock-in amplifier voltage was recorded to give an initial value for this quantity. The shutter was then opened for approximately 10 s and a second lock-in amplifier voltage was recorded. The difference in these two voltages was the lock-in amplifier signal due to heating of the solutions. The solutions were allowed to cool for at least one minute before another measurement was taken.

Figure 2:
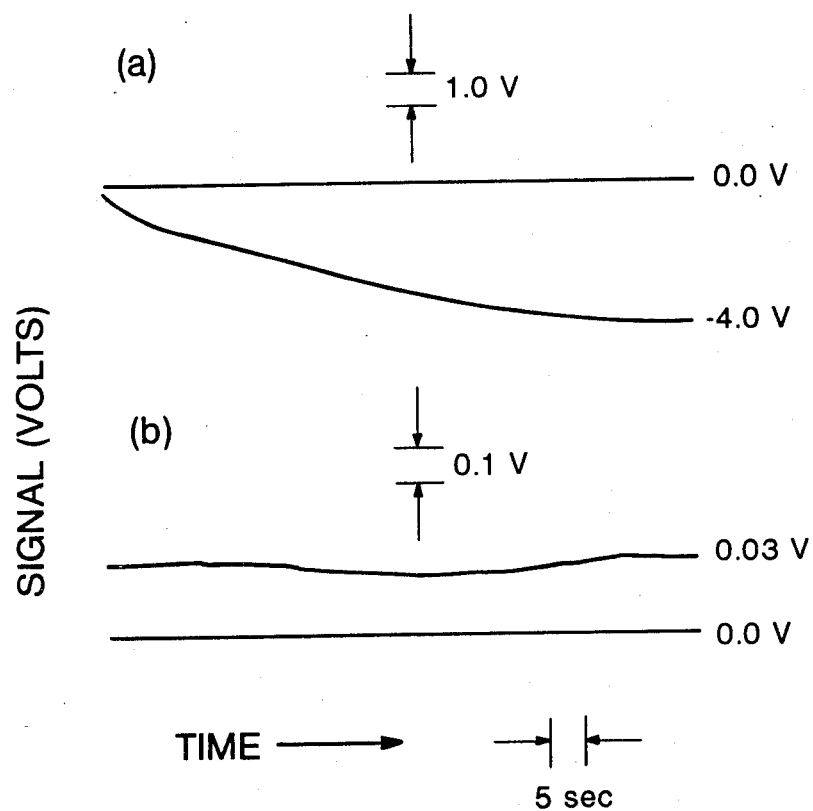
FIG. 2 shows the effect of stabilizing the reference fringe pattern with respect to drift in the probe fringe pattern, curve (a) showing the drift of the probe fringes relative to a baseline with the stabilization circuitry off, while curve (b) shows the drift relative to a baseline with stabilization circuitry activated.

FIG. 2 shows the drift of the probe fringe pattern with the stabilization circuitry on and off. The curves represent the lock-in amplifier signal over a period of approximately 80 s. The straight horizontal lines are the baselines; about 0 V. Curve (a) describes the drift of the probe fringe pattern with the stabilization circuitry off. This drift is approximately $-4$ V. Curve (b) is the drift of the fringes with the stabilization circuitry on. It is apparent that with the fringes stabilized, the amount of drift is reduced by a factor greater than 100.

The response of the apparatus to a change in the optical pathlength of one probe beam through the interferometer was investigated using a second galvanometer-driven compensator plate. That is, the relationship between the probe fringe intensity as viewed through the hole in the screen, hereinafter referred to as signal intensity, and the change in optical pathlength of the probe beams through the interferometer was determined by varying the rotation angle of the compensator plate which changes the optical pathlength in a predictable manner. A linear relationship was found between the change in optical pathlength and the signal intensity, which indicates that this signal intensity, which is related to the lock-in amplifier output voltage, is directly proportional to the difference in optical absorptivity between the samples, $\Delta\alpha$. This later relationship can be proven theoretically and holds for values of optical pathlength changes of up to at least $3\times10^{-6}$ cm. For very large changes in optical pathlength, this linear relationship breaks down. However, this is not a serious limitation because the response of the apparatus to a change in optical pathlength can be easily calibrated.

Figure 3:
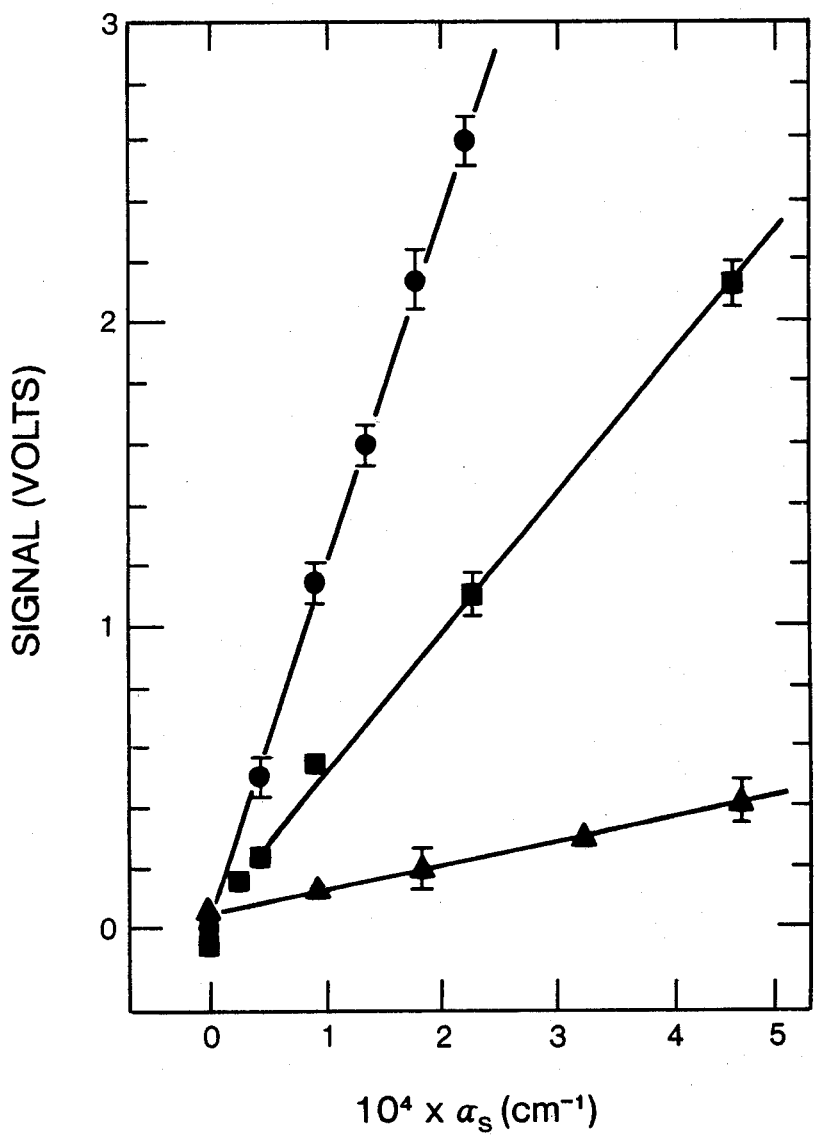
FIG. 3 shows the change in phase-sensitive detector signals, which is related to the change in the probe fringe pattern position, versus the change in solute absorptivity ($\alpha_s$) for three solvents: water ($\triangle$); CH$_3$OH ($\square$); and CCl$_4$ (O).

FIG. 3 shows the lock-in amplifier signal versus the change of solute absorptivity, $\alpha_s$, for three solvents; water ($\triangle$); methanol ($\square$); and carbon tetrachloride ($\bigcirc$). Small additional amounts of solute were added to the solution in one sample cell in the interferometer to produce a differential response. The methanol data were obtained with a background absorption of $2.3\times10^{-3}$ cm$^{-1}$ in each cell. The data for water and carbon tetrachloride were obtained using the background absorption of the pure solvent. For water this was about $3\times10^{-4}$ cm$^{-1}$, and for carbon tetrachloride about $1.2\times10^{-5}$ cm$^{-1}$. The heating laser power was about 50 mW for both carbon tetrachloride and methanol, and about 100 mW for water. The solutes employed were cobalt sulfate for water and methanol, and iodine for carbon tetrachloride, and the lock-in amplifier readings were taken 10 s after the argon-ion laser beam was unblocked. The predicted linear relationship between the difference in optical absorptivity between the two samples and the lock-in amplifier signal is confirmed for the three solutions employed.

Figure 4:
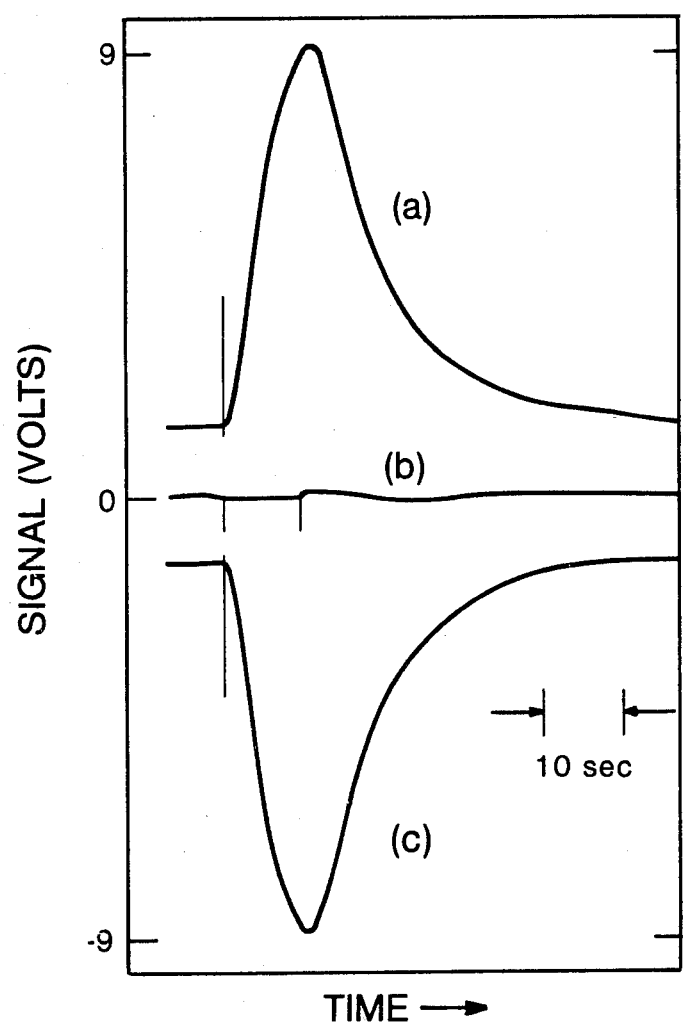
FIG. 4 shows the comparison of phase-sensitive detector signals, which are related to the shift in the probe fringe pattern, with the instant apparatus in a non-differential (curves (a) and (c)), and differential (curve (b)) configuration.

FIG. 4 shows the comparison of lock-in amplifier signals with the instant apparatus in a non-differential mode of operation (curves (a) and (c)), and a differential mode of operation (curve (b)), and shows the ability of this apparatus to null out absorptions of equal strength. In curve (a), one cell contains pure methanol, with an absorptivity of approximately $1.5 \times 10^{-4}$ cm$^{-1}$, and the other cell contains a cobalt sulfate/methanol solution having an absorptivity at (515 nm of about $2.3 \times 10^{-3}$ cm$^{-1}$). In curve (b), both cells contain the cobalt sulfate/methanol solution having an absorptivity at 515 nm of about $2.3 \times 10^{-3}$ cm$^{-1}$, and shows the ability of the instant apparatus to null out absorptions of equal strength in the differential interferometer mode of operation. In curve (c), the solutions in curve (a) are interchanged between the two cells. The initial spike on each curve indicates the start of the heating of the solutions when the argon-ion laser beam is unblocked. The heating period lasts for approximately 10 s. Typically, signals due to the background absorptions could be nulled out to better than one part in 400. The null signals in these cases were on the order of the normal drift of the interferometer over a period of about 10 s; that is, approximately 0.02 volts.

Figure 5:
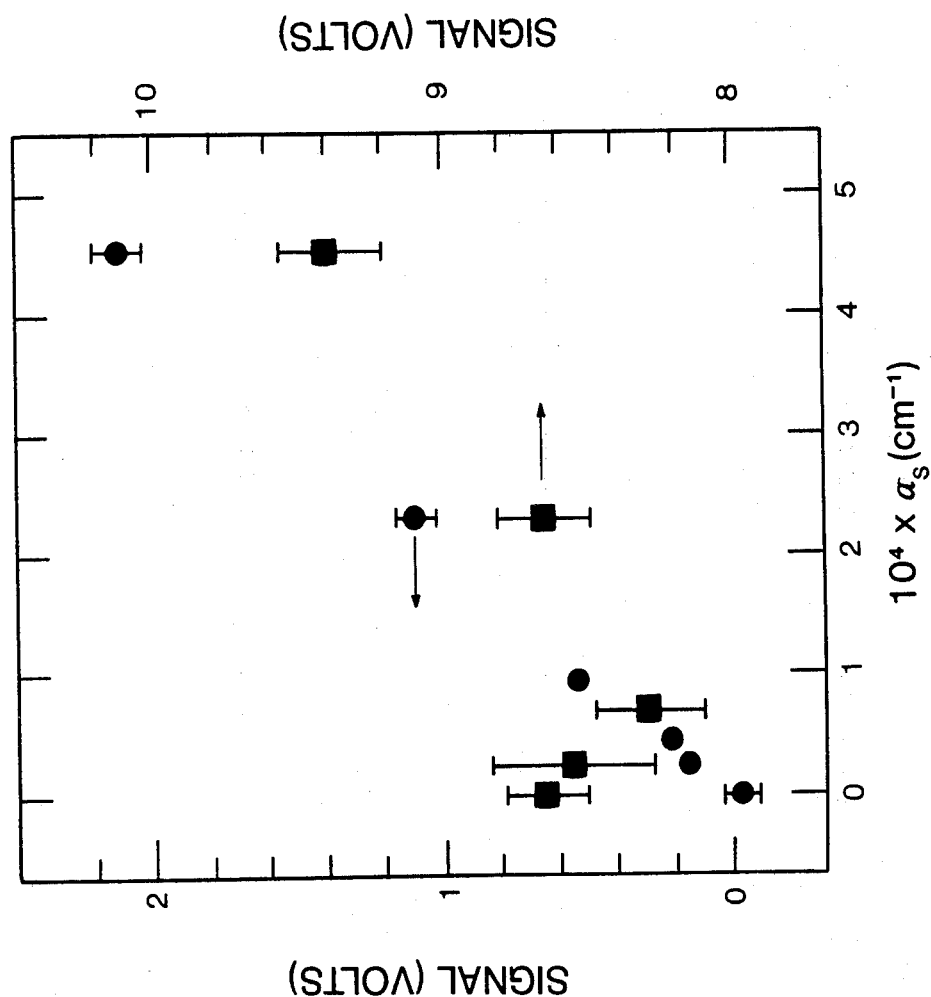
FIG. 5 compares absorptivity measurements with the apparatus in a differential (O) and non-differential ($\square$) configuration with respect to measurement precision as reflected in the precision bars and different ordinate scales.

FIG. 5 shows a comparison of differential (O) and non-differential (□) measurements of solute absorptions ranging between $(0.23-4.6) \times 10^{-4}$ cm$^{-1}$ in the presence of a background absorption of $2.3 \times 10^{-3}$ cm$^{-1}$. For the differential measurements, the background absorption of each solution was adjusted to be initially $2.3 \times 10^{-3}$ cm$^{-1}$. Small amounts of a concentrated solution of CoSO$_4$/CH$_3$OH were then added to one cell to generate a differential signal. For the non-differential measurements, one cell contained pure methanol and small amounts of the concentrated solution were added to the other cell which had a minimum background absorption of $2.3 \times 10^{-3}$ cm$^{-1}$. In both cases, the background absorption was provided by cobalt sulfate dissolved in methanol. The reduction in noise of the differential data, which is evidenced by the very much smaller precision bars on the data points, clearly demonstrates the superiority of nulling out background absorptions in order to measure solute absorptions that are significantly smaller.

Figure 6:
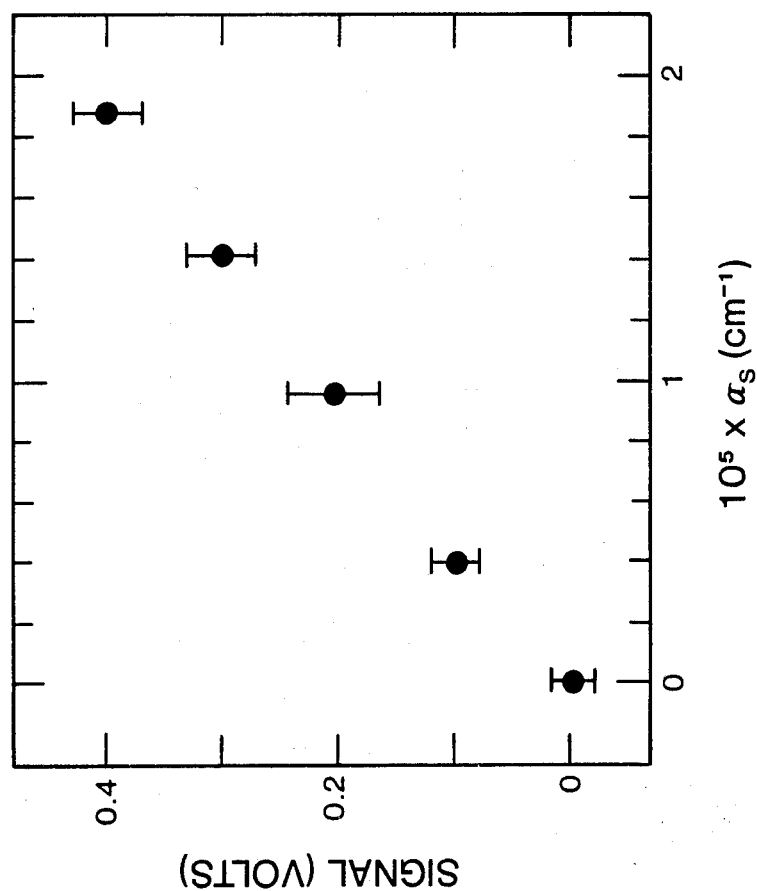
FIG. 6 is a demonstration that the smallest absorptivity measurable with an embodiment of the instant invention is approximately $5 \times 10^{-6}$ cm$^{-1}$ for solutions of iodine in carbon tetrachloride the latter solvent an absorptivity of approximately $1.2 \times 10^{-5}$ cm$^{-1}$.

FIG. 6 shows the investigation of the detection limit of the interferometer for carbon tetrachloride. Solute absorptions of $\sim 5 \times 10^{-6}$ cm$^{-1}$ could be detected (with signal-to-noise ratio of approximately 2) using laser powers of approximately 100 mW. The absorptivity of CCl$_4$ at 515 nm is listed in the literature as $1.2 \times 10^{-5}$ cm$^{-1}$ which was the background absorption in each cell. Using methanol and a laser power of about 50 mW, increases in absorptivity of one cell of approximately $2 \times 10^{-5}$ cm$^{-1}$ could be detected in the presence of a background absorption of $2.3 \times 10^{-3}$ cm$^{-1}$. The poorest detection limit was found for water. For a laser power of approximately 100 mW, the smallest solute absorptivity measurable was about $3 \times 10^{-4}$ cm$^{-1}$ for this solvent. The difference in detection limits is a result of the different thermooptic sensitivities of the various solvents; for example, the change in refractive index of water with temperature is very much smaller than, say, carbon tetrachloride.

The solution cells, wedged plates, and dielectric-coated dichroic mirrors inside of the interferometer were made of fused quartz which has a smaller optical absorption than pyrex or glass. Reference 1 indicates that it is especially important that the solution cells be made of fused quartz (or other weakly absorbing transparent material) because pyrex cell windows absorb some of the heating laser beam energy which is passed on to the liquid, resulting in a transient signal resembling actual absorption of the laser light by the solution. Even quartz cells may produce noticeable heating of the solutions at increased laser powers or when small absorptivities are measured ($<10^{-5}$ cm$^{-1}$). To a first approximation, however, in the differential measurements of the instant invention these effects are to a good degree nulled out. Dilute solutions were generally prepared from more concentrated solutions by simple volumetric dilution. These dilute solutions were then pipetted into the sample cells which remained in a fixed position inside the interferometer. It was necessary to wait about 10 to 15 minutes before making measurements to allow turbulence and thermal gradients within the samples to subside. A total of 12 measurements were taken with each solution. The total length of the precision bars shown in the figures here and above is twice the standard deviation.

The null response of the apparatus of the instant invention was found to exceed the limits attributable to normal drift of the signal under two separate conditions: (1) use of heating laser powers greater than about 100 mW, regardless of the solution absorptivity, and (2) when the power absorbed by the solution exceeds approximately $1.5 \times 10^{-4}$ W/cm. The first condition was caused by heating of the optical components in the interferometer and may be avoidable with a different arrangement of the components (e.g., moving the wedges to a position after the grating so that they do not intercept the heating beams). It was not possible to single out any particular component (s) as being the main source of the signal at increased laser powers. The second condition is the result of convection and/or thermal lensing. Thermal lensing, which reduces the on-axis intensity of the probe beam, may be a source of spurious signals in our detection system because a change in probe intensity at the photodetector results in a lock-in amplifier signal resembling a fringe shift. Thermal lensing was not important in the experiments reported hereinabove, however, because the laser beams were not focused into the solution cells as in thermal lensing experiments. At increased laser powers and/or absorptivities, though, thermal lensing could become noticeable without focusing.

It should be mentioned at this point that the measured signal intensity derived from the instant interferometer is strongly dependent upon the quantum yield for conversion of absorbed laser radiation into heat in the solution. Generally, this quantum yield is near unity in which case the measured absorptivity and measured absorptivity differences reflect the true absorptivity. In the situation where this does not obtain; that is, the quantum yield is substantially less than unity, appropriate corrections must be made when quoting measured absorptivities.

Also to be noted is that since different materials exhibit different temporal thermal responses, it is imperative that the major constituent of the samples in each arm of the interferometer be identical.

It has been demonstrated that the interferometer is an effective method of nulling large background absorptions due to solvent or solute. In the differential mode of the interferometer, the signal that would be produced by the interferometer in the non-differential configuration was suppressed by a factor of about 400. With the background signals suppressed, differences in absorptivities between the cells ~1/100th of background were measured. In addition, the smallest absorption measured with the interferometer was approximately $5 \times 10^{-6}$ cm$^{-1}$, which is comparable to that actually measured using other thermooptic techniques. The principal advantages of differential interferometry are:

(1) the method has a detection limit comparable to that demonstrated for other thermooptic-based techniques;

(2) the physical principles which produce the signal are easily analyzed and do not increase in complexity in going from a non-differential to a differential configuration of the apparatus;

(3) the only critical alignment of the apparatus is the superimposing of the axes of propagation of the heating and probe laser beams;

(4) the long term stability of the apparatus of the instant invention is very good (~1 week). The technique is insensitive to small variations in laser beam profile; and (5) the apparatus of the instant invention is especially useful for recording differential thermooptic spectra of solutions. The use of probe beams separate from heating beams to record the thermooptic signal permits scanning of the heating laser wavelength without the problem of phase-shifts and beam diffraction introduced by dispersion in optical elements through which the beams pass. Since the wavelength of the probe beam is fixed, a phase-shift occurs only due to the heating of the solutions.

The foregoing description of a preferred embodiment of the invention have been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring small differences between weak optical absorptions of samples comprising solutions of solutes in substantially identical solvents using differential interferometry and the conversion of absorbed radiation into heat for the solute, which comprises the steps of:

a. splitting each of a narrowly-spatially displaced parallel probe laser beam and a reference laser beam incident on the interferometer into a pair of parallel travelling beams hereinafter referred to as first and second probe laser beam and first and second reference laser beam, said first probe laser beam and said first reference laser beam emerging narrowly spaced and approximately parallel, and said second probe laser beam emerging widely spaced from said first probe laser beam and narrowly spaced from and approximately parallel to said second reference laser beam;

b. adjusting said first and second probe beams to be of approximately equal intensity;

c. adjusting said first and second reference beams to be of approximately equal intensity;

d. inserting a light-transmitting sample holding cell into the path of said narrowly spaced first probe and reference laser beams, hereinafter referred to as cell one;

e. inserting a light-transmitting sample holding cell into the path of said narrowly spaced second probe and reference laser beams, hereinafter referred to as cell two;

f. recombining said first probe laser beam and said second probe laser beam to form an interference fringe pattern hereinafter referred to as probe fringe pattern;

g. recombining said first reference laser beam and said second reference laser beam to form an interference fringe pattern hereinafter referred to as reference fringe pattern;

h. introducing a first sample into cell one and a second sample into cell two;

i. superimposing a first amplitude modulated heating laser beam colinear with said first probe laser beam such that said first heating laser beam enters said cell one after said superposition j. superimposing a second amplitude modulated heating laser beam colinear with said second probe laser beam such that said second heating laser beam enters said cell two after said superposition;

k. adjusting the intensity of said first heating laser beam entering said cell one to be substantially equal to that of said second heating laser beam entering said cell two;

l. correcting for loss of parallelism, if any, of said first probe laser beam with said second probe laser beam and of said first reference laser beam with said second reference laser beam due to their passing through wedged components in the interferometer which introduce non-parallel travel, respectively;

m. stabilizing said reference fringe pattern with respect to drift due to air currents, variations in room temperature, and thermal gradients in said first sample and said second sample, which also stabilizes said probe fringe pattern;

n. monitoring the position of said probe fringe pattern to determine any position shift due to any difference in the thermooptic heating of the sample in said cell one relative to said cell two which changes said optical pathlength of said first probe laser beam relative to said second probe laser beam when said first heating laser beam is allowed to pass through said cell one for a specified period of time and simultaneously said second heating laser beam is allowed to pass through said cell two for an identical specified period of time, such heating being related to the difference in total absorptivity of the samples in said cell one and said cell two;

o. establishing a calibration curve of said probe fringe position versus difference in measured optical absorption between said first sample and said second sample using a multiplicity of samples of different absorptivities and having known conversion efficiency of laser radiation into heat, generally selected to be unity, and scaling therefore to correct said measured absorptivity difference to equal the true absorptivity difference in the event that said conversion efficiency is less than unity;

p. relating said probe fringe position for the samples under investigation in each of said cell one and said cell two to the difference in optical absorptivity between the two samples, using said first calibration curve, and correcting for any difference from unity of the efficiency of conversion of absorbed laser radiation by the solute under investigation into heat.

2. The method as described in claim 1, wherein a waiting period of time is introduced to allow turbulence and thermal gradients within said samples to subside before said heating beams are allowed to pass through said sample cells.

3. The method as described in claim 2, wherein said heating laser beams superimposed on said probe laser beams are introduced into the interferometer after said splitting step and removed before said recombining step.

4. The method as described in claim 3, wherein said narrowly spaced first probe beam and said first reference beam, and said narrowly spaced second probe beam and said second reference beam are each approximately 5 mm apart.

5. The method as described in claim 4, wherein said specified heating time period is approximately 10 s.

6. The method as described in claim 5, wherein the samples are allowed to cool for a period of approximately one minute before said specified heating time period is begun again in order to make another absorptivity determination.

7. The method as described in claim 6, wherein said stabilizing step for said reference fringe pattern is accomplished using a fringe position detector, feedback electronics, and a driven compensator plate which intercepts said first probe and said first reference laser beam.

8. The method as described in claim 7, wherein said splitting and recombining steps are performed using a Jamin interferometer design in order to make the sensitivity of the absorptivity difference measurements to vibrations minimal.

9. The method as described in claim 8, wherein said incident probe laser beam and said incident reference laser beam include helium-neon laser output.

10. The method as described in claim 9, wherein said first heating laser beam and said second heating laser beam include argon-ion laser output.

11. The method as described in claim 10, wherein said specified heating time period is obtained using a shutter to simultaneously block said first heating laser beam and said second heating laser beam.

12. An apparatus for measuring small differences between weak optical absorptions of sample comprising solutions of solutes in substantially identical solvents using differential interferometry and the conversion of absorbed radiation into heat for the solute, which comprises in combination:
   a. a probe laser beam;
   b. a reference laser beam approximately parallel to and narrowly-spaced from said probe laser beam;
   c. a first amplitude controlled heating laser beam;
   d. a second amplitude controlled heating laser beam;
   e. an interferometer, which further comprises:
      i. a first laser transmitting block to split said probe laser beam and said reference laser beam incident thereon into a first probe beam and a second probe beam, and a first reference beam and a second reference beam, respectively, said first probe beam and said first reference beam emerging approximately parallel and narrowly-spaced and widely-spaced from said second probe beam which emerges approximately parallel to and narrowly-spaced from said second reference beam;
      ii. means for adjusting the intensity of said first and second probe beams and said first and second reference beams; and
      iii. a second laser transmitting block to recombine said first probe beam and said second probe beam, and said first reference beam and said second reference beam to form a probe fringe pattern and a reference fringe pattern, respectively, the position of said fringe patterns reflecting any differential change between the optical pathlengths of said first and second probe beams and said first and second reference beams as they traverse the space between said first and second laser transmitting blocks,
      iv. means for making colinear said first and said second heating laser beams with said first and second probe laser beams, respectively;
      v. means for equalizing the intensity of said first and second heating laser beams after they have emerged from said colinear making means;
      vi. means for correcting any non-parallel deviations of said first probe and reference laser beams, and said second probe and reference laser beams, if necessary, to insure that said first and second probe beams and said first and second reference beams are colinear when recombined in said second laser transmitting block;
      vii. two sample cells hereinafter to be identified as cell one and cell two, which contain the samples under investigation, and through which said first probe beam colinear with said first heating laser beam and said first reference beam narrowly separated from said first probe beam, and said second probe beam colinear with said second heating laser beam and said second reference beam narrowly separated from said second probe beam pass, respectively, after leaving said heating laser intensity equalizing means;
      viii. means for stabilizing said reference fringe pattern with respect to drift due to air currents, variations in room temperature, and thermal gradients in said sample cells which also simultaneously stabilizes said probe fringe pattern with respect to said drift;
      ix. means for detecting the position of said probe fringe pattern which pattern shifts due to the thermooptic effect induced by said heating beams in the samples, which can be related to the difference in optical absorptivity of the two samples under investigation.

13. The apparatus as described in claim 12 wherein a means is introduced for separating said first probe laser beam from said first heating laser beam and said second probe laser beam from said second heating laser beam after said beams have passed through said cell one and cell two, respectively, and colinear making means is located after said first laser transmitting block.

14. The apparatus as described in claim 13, wherein said first and second heating and probe laser beam colinear making means includes a first mirror for said first probe and heating laser beams and a second mirror for said second probe and heating laser beams, said first and second mirrors being substantially transparent to said probe laser beams and substantially reflective to said heating laser beams.

15. The apparatus as described in claim 14, wherein a means is introduced for adjusting said first probe laser beams optical pathlength in order to adjust said probe beam fringe pattern incident upon said detecting means.

16. The apparatus as described in claim 15, wherein said interferometer is of Jamin design to reduce sensitivity to vibrations.

17. The apparatus as described in claim 16, wherein said first and second probe beam and said first and second reference beam intensity adjusting means includes neutral density filters to give maximum visibility of said probe and reference fringe patterns, respectively.

18. The apparatus as described in claim 17, wherein said means for equalizing the intensity of said first and second heating laser beams includes rotatable laser light transparent plates to control the amount of light reflected out of each of said heating beams.

19. The apparatus as described in claim 18, wherein said non-parallel beam correcting means includes a pair of wedged quartz plates located such that they intercept said first probe and reference laser beams.

20. The apparatus as described in claim 19, wherein said heating laser beam separating means includes a diffraction grating.

21. The apparatus as described in claim 20, wherein said reference fringe stabilizing means further comprises:
   i. a driven compensator plate which is part of a closed feedback loop and which changes the optical pathlength of said second reference beam relative to said first reference beam as said second reference beam traverses it, said driven compensator plate also intersecting and changing the optical pathlength of said second probe laser beam;
   ii. modulation means applied to said compensator plate to provide modulation of said reference fringe pattern such that phase-sensitive detection can be used to correct for drift due to air currents, variations in room temperature, and thermal gradients in said sample cells;
   iii. a first phase-sensitive detection means;
   iv. a photodetector;
   v. a negative lens;
   vi. a screen containing a hole through which part of said reference fringe pattern passes and which is located in front of said photodetector; and
   vii. compensator driver control electronics.

22. The apparatus as described in claim 21, wherein said first probe laser beam optical pathlength adjusting means includes a manually rotated compensation plate.

23. The apparatus as described in claim 22, wherein said probe fringe pattern intensity detecting means comprises:
   i. a photomultiplier tube;
   ii. a screen containing a hole through which part of said probe fringe pattern passes, and which is located in front of said photomultiplier tube;
   iii. a second phase-sensitive detection means which is calibrated such that its output can be related to changes in said optical pathlength of said first probe beam relative to said second probe beam, and which responds at the frequency of said modulation means; and
   iv. recording means.

24. The apparatus as described in claim 23, wherein said first probe beam and said first reference beam, and said second probe beam and said second reference beam are displaced by approximately 5 mm.

25. The apparatus as described in claim 24, wherein said first and second heating laser beams include approximately equally divided 515 nm output from a single argon-ion laser.

26. The apparatus as described in claim 25, wherein said probe and reference laser beams include approximately equally divided output from a single helium-neon laser.

27. The apparatus as described in claim 26, wherein said dielectric coated mirrors include dielectric coated mirrors with coatings about 99% reflective at 515 nm, and about 66% transmitting at 633 nm.

28. The apparatus as described in claim 27, wherein said wedged quartz plates include plates with approximately 30 minute wedges.

29. The apparatus as described in claim 28, wherein said heating laser beam amplitude control includes a manually operated shutter.

* * * * *